(12) United States Patent
Be'er et al.

(10) Patent No.: US 7,512,524 B2
(45) Date of Patent: Mar. 31, 2009

(54) PREPARING PEPTIDE SPECTRA FOR IDENTIFICATION

(75) Inventors: Ilan Be'er, Haifa (IL); Eilon Barnea, Nesher (IL); Emanuel Gofman, Haifa (IL)

(73) Assignee: International Business Machines Corporation, Armonk, NY (US)

( * ) Notice: Subject to any disclaimer, the term of this patent is extended or adjusted under 35 U.S.C. 154(b) by 626 days.

(21) Appl. No.: 11/084,435

(22) Filed: Mar. 18, 2005

(65) Prior Publication Data

US 2006/0208185 A1    Sep. 21, 2006

(51) Int. Cl.
*G06F 15/00* (2006.01)
(52) U.S. Cl. ...................................... 702/196
(58) Field of Classification Search .................. 702/19, 702/21, 22, 23, 27, 30, 183, 193, 196; 435/6
See application file for complete search history.

(56) References Cited

U.S. PATENT DOCUMENTS

2003/0175760 A1*  9/2003  Walker et al. .................. 435/6
2006/0161814 A1*  7/2006  Wocke et al. ................. 714/26

OTHER PUBLICATIONS

Hurst et al., Mass Spectrometric Detection od Affinity Purified Crosslinked Peptides, 2004, Elsevier Inc.American Society for Mass Spectrometry, pp. 832-839.*

Jain, A.K., et al., "Data Clustering: A Review", ACM Computing Surveys, vol. 31, No. 3, Sep. 1999.

Lance, G. N., et al., "A general theory of classificatory sorting strategies. Hierachical systems", Computer J. 9:373-80, 1967, [Computing Res. Section, CSIRO, Canberra, ACT, Australis].

Zhao, Ying, et al., "Evaluation of Hierarchical Clustering Algorithms for Document Datasets", Proceedings of Int'l Conf. on Information and Knowledge Management, pp. 515-524, 2002.

Kurita, T., et al., "An Efficient Agglomerative Clustering Algorithm for Region Growing", Proceedings of IAPR Workshop on Machine Vision Applications, Dec. 13-15, Kawasaki, pp. 210-213, 1994.

* cited by examiner

*Primary Examiner*—Edward Raymond
*Assistant Examiner*—Mohamed Charioui

(57) ABSTRACT

A method for preparing peptide spectra for identification, the method including constructing a symmetric distance matrix from a plurality of peptide spectra, where a cluster of at least one of the spectra is represented in a row of the matrix, and where the cluster is also represented in a column of the matrix, finding the minimum of each of the clusters in the matrix, constructing a vector from the minima where each element in the vector corresponds to one of the clusters, finding the global minimum of the matrix as being the minimum of the vector, merging two of the clusters identified by the global minimum into a merged cluster, and providing the merged cluster for identification of at least one peptide associated with the merged cluster.

8 Claims, 22 Drawing Sheets

PREPARING PEPTIDE SPECTRA FOR IDENTIFICATION

FIELD OF THE INVENTION

The present invention relates to proteomics in general, and more particularly to preparing peptide spectra for identification.

BACKGROUND OF THE INVENTION

Proteomics is a term used to describe the large-scale study of proteins. Proteins provide a key functional element in biological behavior, however, their exact role is still a matter of research. One popular method of studying proteins is through the comparative study of protein peptides with similar amino acid sequences. In comparative statistical studies, peptides are typically numerically characterized, such as with the aid of a Mass Spectrometer, which provides a digital signature for each peptide. The numerical characterizations of different peptides may then be clustered utilizing a statistical clustering technique, such as Unweighted Pair Group Method with Arithmetic Mean (UPGMA). Peptides whose numerical characterizations are similar may be grouped together in the same cluster. These clusters may then be used to identify the peptides.

In the method shown in FIG. 1, each numerical characterization of a peptide is initially considered to be a cluster having a single member. Given a distance function, a distance matrix D may then be constructed indicating the distances between each pair of clusters. For a given distance matrix D, where dij is the distance between item i and item j, the following iterative procedure is performed:

1. Find $d_{min}=\min(d_{ij})$; If more than one $d_{ij}$ are equal to $d_{min}$, select one of them, typically the min(i,j).
2. If $d_{min}$ is greater than a predefined threshold, such as 0.15 when the distance is normalized between 0 and 1, then stop.
3. Create a new cluster which is the union of clusters i and j.
4. Remove cluster j, and replace cluster i with the new cluster.
5. If D contains only one cluster then stop the iterative procedure.
6. Update the distance entries in D that are affected by the creation of the new cluster.
7. Go to Step 1.

Unfortunately, the process of determining the minimum item in a matrix is computationally expensive and typically requires on the order of O(N2) operations, where D is a symmetric matrix of size N×N. Given the vast numbers of proteins yet to be studied, a method for preparing peptide spectra for identification that requires fewer operations than existing techniques would therefore be advantageous.

SUMMARY OF THE INVENTION

Some embodiments of the present invention disclose a system and method for clustering peptide spectra using a sparse distance matrix in preparation for peptide analysis and identification.

In one aspect of the present invention a method is provided for preparing peptide spectra for identification, the method including a) constructing a symmetric distance matrix from a plurality of peptide spectra, where a cluster of at least one of the spectra is represented in a row of the matrix, and where the cluster is also represented in a column of the matrix, b) finding the minimum of each of the clusters in the matrix, c) constructing a vector from the minima where each element in the vector corresponds to one of the clusters, d) finding the global minimum of the matrix as being the minimum of the vector, e) merging two of the clusters identified by the global minimum into a merged cluster, and f) providing the merged cluster for identification of at least one peptide associated with the merged cluster.

In another aspect of the present invention the method further includes g) finding the minimum of any of the clusters in the matrix where the distance between the cluster and either of the merged clusters was the smallest relative to the distance between the cluster and any other of the clusters, and h) updating any of the elements in the vector for which a minimum was found in step g) for the cluster corresponding to the element.

In another aspect of the present invention the finding step d) includes ordering the elements in the vector in hierarchical order, and identifying the root of the hierarchy as the global minimum.

In another aspect of the present invention the method further includes g) finding the minimum of any of the clusters in the matrix where the distance between the cluster and either of the merged clusters was the smallest relative to the distance between the cluster and any other of the clusters, h) updating any of the elements in the vector for which a minimum was found in step g) for the cluster corresponding to the element, and i) reordering the updated elements in the vector in hierarchical order.

In another aspect of the present invention each of the vector elements is associated with an index of any of the clusters for which the minimum was found with respect to the cluster to which the vector element corresponds.

In another aspect of the present invention the constructing step includes representing the plurality of peptide spectra as a set of multidimensional vectors, ordering the multidimensional vectors, determining the closeness between any two of the ordered vectors in accordance with a measure of closeness, determining the distance between any two of the ordered vectors using a distance function where the vectors are close to each other in accordance with the measure of closeness, and constructing the matrix from the distances.

In another aspect of the present invention the ordering step includes ordering the vectors according to their precursor (parent) mass (PM) of their associated peptide.

In another aspect of the present invention the determining closeness step includes determining that the two vectors are close where their masses are within 2 Daltons of each other.

In another aspect of the present invention a method is provided for constructing a sparse distance matrix of peptide spectra, the method including representing a plurality of peptide spectra as a set of multidimensional vectors, ordering the vectors, determining the closeness between any two of the ordered vectors in accordance with a measure of closeness, determining the distance between any two of the ordered vectors using a distance function where the vectors are close to each other in accordance with the measure of closeness, and constructing a matrix from the distances.

In another aspect of the present invention the ordering step includes ordering the vectors according to their precursor (parent) mass (PM) of their associated peptide.

In another aspect of the present invention the determining closeness step includes determining that the two vectors are close where their masses are within 2 Daltons of each other.

In another aspect of the present invention a system is provided for preparing peptide spectra for identification, the system including a) means for constructing a symmetric distance matrix from a plurality of peptide spectra, where a cluster of at least one of the spectra is represented in a row of the matrix, and where the cluster is also represented in a column of the matrix, b) means for finding the minimum of each of the clusters in the matrix, c) means for constructing a vector from the minima where each element in the vector corresponds to one of the clusters, d) means for finding the global minimum of the matrix as being the minimum of the vector, e) means for merging two of the clusters identified by the global minimum into a merged cluster, and f) means for providing the merged cluster for identification of at least one peptide associated with the merged cluster.

In another aspect of the present invention the system further includes g) means for finding the minimum of any of the clusters in the matrix where the distance between the cluster and either of the merged clusters was the smallest relative to the distance between the cluster and any other of the clusters, and h) means for updating any of the elements in the vector for which a minimum was found in step g) for the cluster corresponding to the element.

In another aspect of the present invention the means for finding d) is operative to order the elements in the vector in hierarchical order, and identify the root of the hierarchy as the global minimum.

In another aspect of the present invention the system further includes g) means for finding the minimum of any of the clusters in the matrix where the distance between the cluster and either of the merged clusters was the smallest relative to the distance between the cluster and any other of the clusters, h) means for updating any of the elements in the vector for which a minimum was found in step g) for the cluster corresponding to the element, and i) means for reordering the updated elements in the vector in hierarchical order.

In another aspect of the present invention each of the vector elements is associated with an index of any of the clusters for which the minimum was found with respect to the cluster to which the vector element corresponds.

In another aspect of the present invention the means for constructing is operative to represent the plurality of peptide spectra as a set of multidimensional vectors, order the multidimensional vectors, determine the closeness between any two of the ordered vectors in accordance with a measure of closeness, determine the distance between any two of the ordered vectors using a distance function where the vectors are close to each other in accordance with the measure of closeness, and construct the matrix from the distances.

In another aspect of the present invention the means for ordering is operative to order the vectors according to their precursor (parent) mass (PM) of their associated peptide.

In another aspect of the present invention the means for determining closeness is operative to determine that the two vectors are close where their masses are within 2Daltons of each other.

In another aspect of the present invention a system is provided for constructing a sparse distance matrix of peptide spectra, the system including means for representing a plurality of peptide spectra as a set of multidimensional vectors, means for ordering the vectors, means for determining the closeness between any two of the ordered vectors in accordance with a measure of closeness, means for determining the distance between any two of the ordered vectors using a distance function where the vectors are close to each other in accordance with the measure of closeness, and means for constructing a matrix from the distances.

In another aspect of the present invention the means for ordering is operative to order the vectors according to their precursor (parent) mass (PM) of their associated peptide.

In another aspect of the present invention the means for determining closeness is operative to determine that the two vectors are close where their masses are within 2Daltons of each other.

In another aspect of the present invention a computer program is provided embodied on a computer-readable medium, the computer program including a first code segment operative to construct a symmetric distance matrix from a plurality of peptide spectra, where a cluster of at least one of the spectra is represented in a row of the matrix, and where the cluster is also represented in a column of the matrix, a second code segment operative to find the minimum of each of the clusters in the matrix, a third code segment operative to construct a vector from the minima where each element in the vector corresponds to one of the clusters, a fourth code segment operative to find the global minimum of the matrix as being the minimum of the vector, a fifth code segment operative to merge two of the clusters identified by the global minimum into a merged cluster, and a sixth code segment operative to provide the merged cluster for identification of at least one peptide associated with the merged cluster.

In another aspect of the present invention a computer program is provided embodied on a computer-readable medium, the computer program including a first code segment operative to represent a plurality of peptide spectra as a set of multidimensional vectors, a second code segment operative to order the vectors, a third code segment operative to determine the closeness between any two of the ordered vectors in accordance with a measure of closeness, a fourth code segment operative to determine the distance between any two of the ordered vectors using a distance function where the vectors are close to each other in accordance with the measure of closeness, and a fifth code segment operative to construct a matrix from the distances.

BRIEF DESCRIPTION OF THE DRAWINGS

The present invention will be understood and appreciated more fully from the following detailed description taken in conjunction with the appended drawings in which.

DETAILED DESCRIPTION OF PREFERRED EMBODIMENTS

Figure 1:
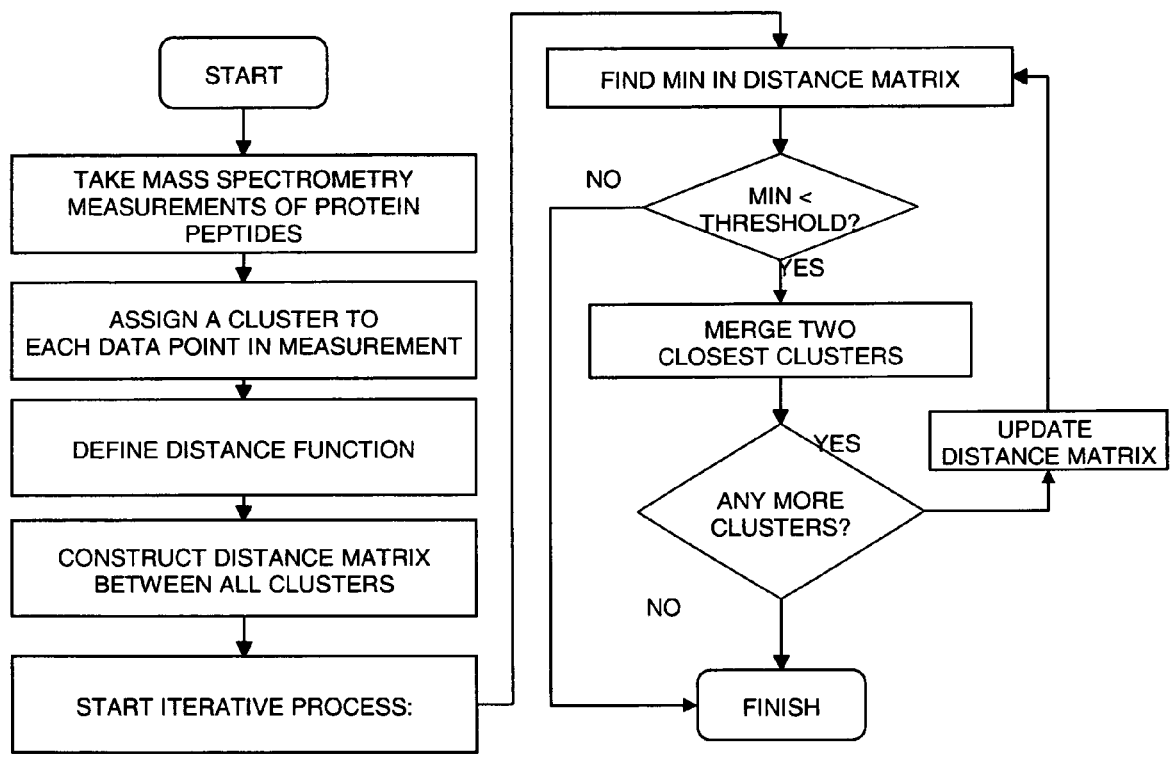
FIG. 1 is a simplified flowchart illustration of a method for preparing peptide spectra for identification, useful in understanding the present invention.
Figure 2A:
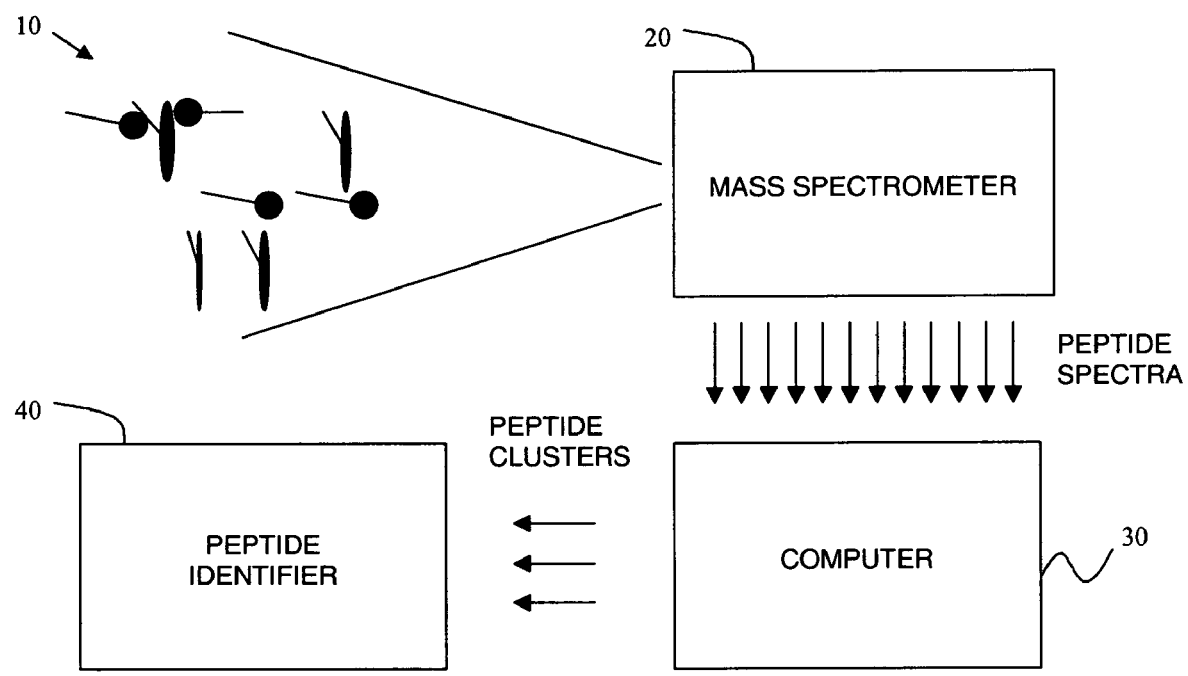
FIG. 2A is a simplified pictorial illustration of a system for preparing peptide spectra for identification, constructed and operative in accordance with an embodiment of the present invention.
Figure 2B:
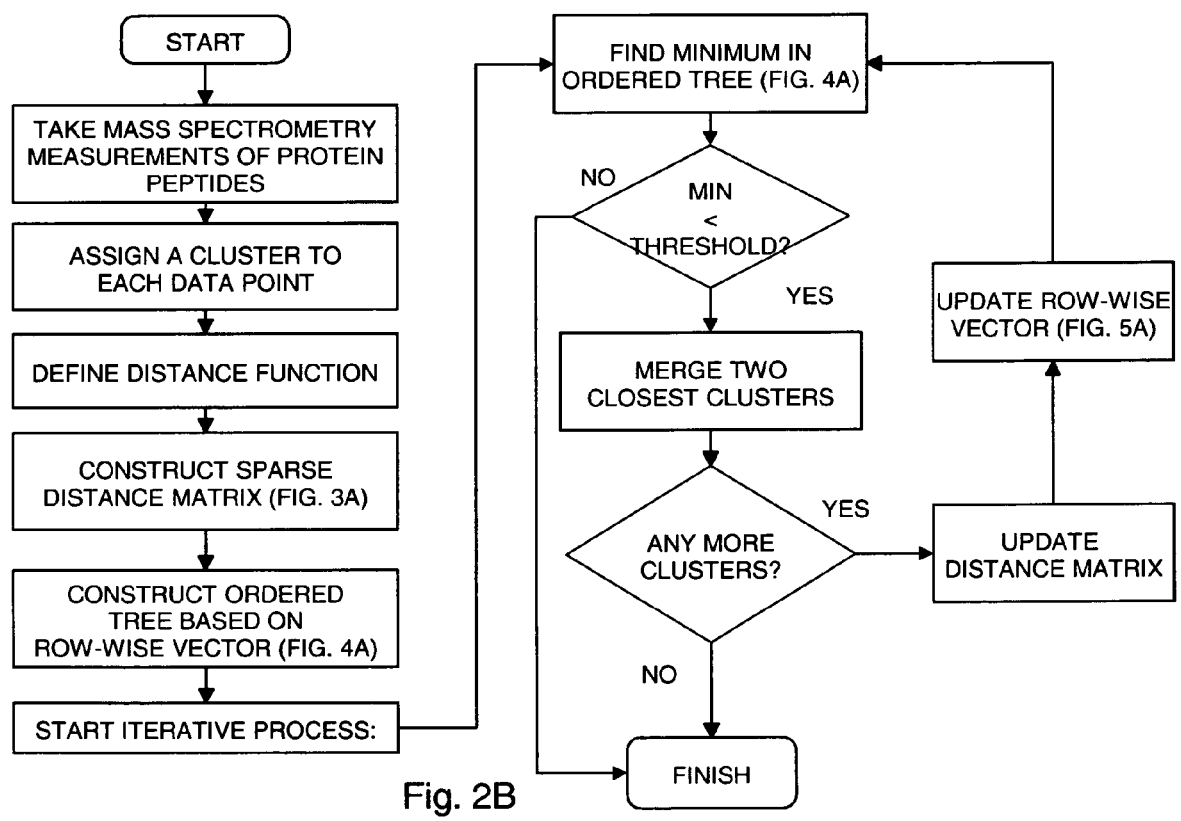
FIG. 2B is a simplified flowchart illustration of a method for preparing peptide spectra for identification, operative in accordance with an embodiment of the present invention.

Reference is now made to FIG. 2A, which is a simplified pictorial illustration of a system for preparing peptide spectra for identification, constructed and operative in accordance with an embodiment of the present invention, and to FIG. 2B, which is a simplified flowchart illustration of a method for clustering peptides with similar characteristics, operative in accordance with an embodiment of the present invention. In the system and method of FIGS. 2A and 2B, peptides 10 are typically numerically characterized, such as with the aid of a Mass Spectrometer 20, which provides a digital signature for each peptide. The numerical characterizations of different peptides may then be clustered on a computer 30, such as by using the method described hereinbelow with reference to FIG. 2B, where a sparse distance matrix is constructed, such as using the method that is described hereinbelow with reference to FIG. 3A, and a row-wise vector is used to find the minimum of the matrix, such as may be constructed using the method that is described hereinbelow with reference to FIG. 4A. During an iterative process the minimum in the distance matrix is preferably found with the aid of the row-wise vector, and modifications to the distance matrix are preferably made to the matrix and to the row-wise vector as described hereinbelow with reference to FIG. 5A through 5C. Thus, the method of FIG. 2A includes the following steps:

1. Create a sparse distance matrix, preferably as described hereinbelow with reference to FIG. 3A.
2. Calculate the minimum for each row in D, preferably storing the minimum and the index of its column in a vector of pairs $V_i = \{d_{i\ min}, j\}$, where the first component of $V_i$ is the minimum value in row i, and the second component of $V_i$ is the index to the corresponding cluster, being the cluster which is nearest to cluster i.
3. Order V, such as by performing an ordering similar to heap sorting, preferably as described hereinbelow with reference to FIG. 4A.
4. Analyze V to find the minimum in the entire distance matrix D, which indicates the two closest clusters.
5. Stop the iterations if the minimum value exceeds a predefined threshold, such as 0.15 when the distance is normalized between 0 and 1.
6. Update D by merging the two clusters that are closest to each other.
7. Stop the iterative procedure once a predefined stop condition is met, such as when D contains only one cluster.
8. Update the entries in D that are affected by the merge.
9. Update V, preferably as described hereinbelow with reference to FIGS. 5A, 5B and 5C.
10. Go to step 4.

Once the desired stop condition is reached, the cluster's representative spectra may then be used by a peptide identifier 40 to identify the peptides using conventional techniques.

Figure 3A:
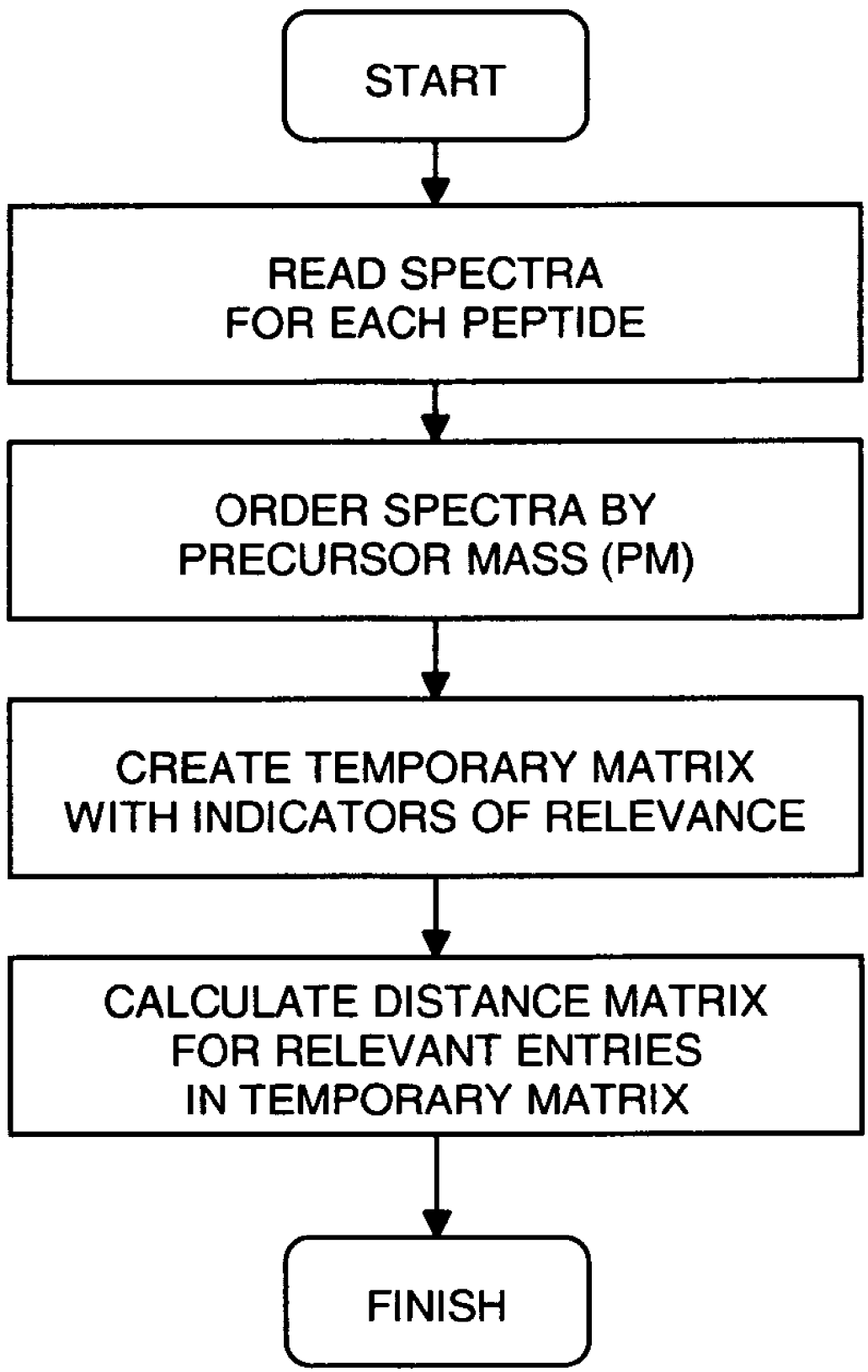
FIG. 3A is a simplified flowchart illustration of a method for constructing a sparse distance matrix, operative in accordance with an embodiment of the present invention.
Figure 3B:
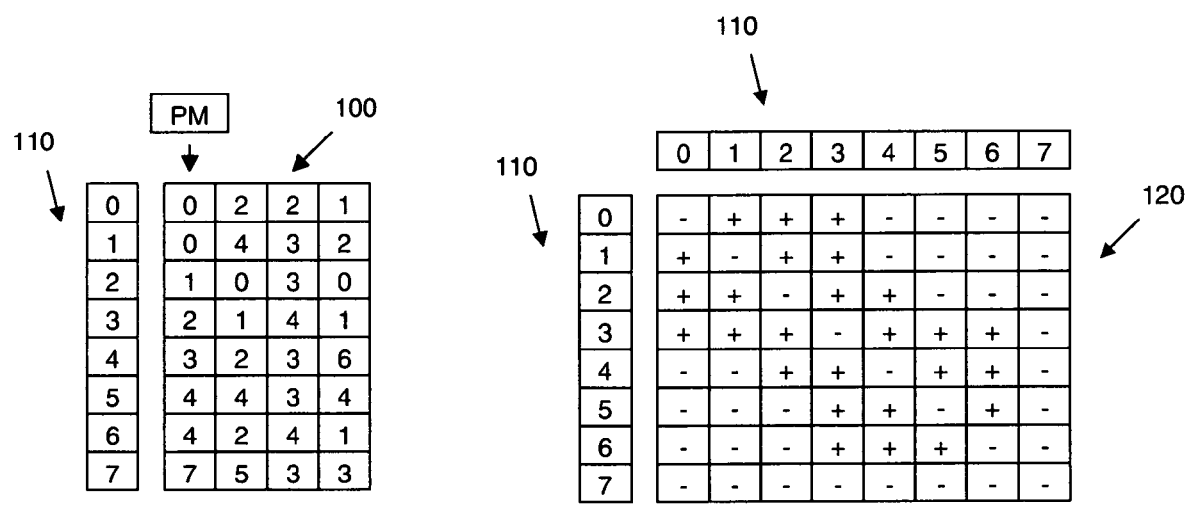
FIGS. 3B and 3C are exemplary distance matrices, constructed and operative in accordance with an embodiment of the present invention.
Figure 3C:
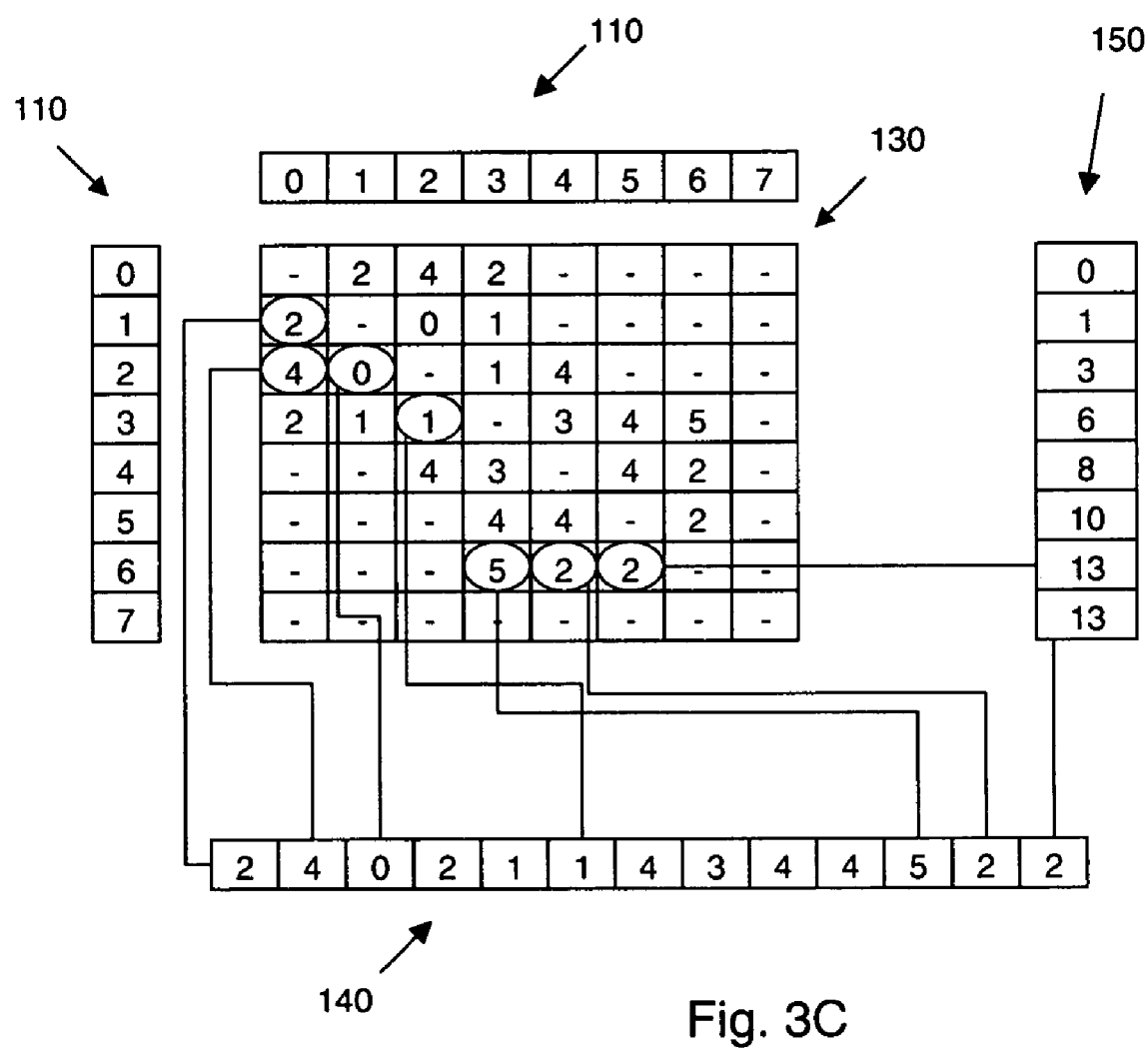

Reference is now made to FIG. 3A, which is a simplified flowchart illustration of a method for constructing a sparse distance matrix, operative in accordance with an embodiment of the present invention, and to FIGS. 3B and 3C, which are exemplary distance matrices, constructed and operative in accordance with an embodiment of the present invention. In the method of FIG. 3A, a distance function is preferably defined to cluster items, such as peptides characterized by their Mass Spectrum. For example, the following distance function measures the distance between two peptide spectra, k and l, by calculating the cosine of the angle between the multidimensional vectors representing the spectra:

$$d_{kl} = 1 - \mathrm{sum}_i(I_{ki} * I_{li}) / (sqrt(\mathrm{sum}_i(I_{ki} * I_{ki}) * \mathrm{sum}_i(I_{li} * I_{li})),$$

where $I_{ki}$ is the intensity of spectra k at element i with mass $m_i$. For the sake of simplicity, it may be assumed that mass values $m_i$ for the same i are equal in all spectra, or dummy mass points may be inserted with corresponding intensity values equal to 0.

A set of spectra is typically represented as a set of multidimensional vectors, where each vector is represented as a separate row in matrix 100 in FIG. 3B. In the method of FIG. 3A, a spectral value, such as the precursor (parent) mass (PM) of the peptide, is preferably chosen to order the vectors within matrix 100. For example, in FIG. 3B, the PM is shown as the first component of the vector. The vectors are then ordered in ascending order by the PM and labeled column-wise and row-wise with a set of cluster numbers 110.

A temporary matrix 120 is preferably constructed, where each element located at column i and row j of temporary matrix 120 may have either a '+' indicating that the relationship between peptide spectra indexed by i is relatively close to the peptide spectra indexed by j, or a '−' indicating that the element indexed by i is not close to the element indexed by j, where closeness is preferably determined using a measure of closeness between the PM of the elements. Elements that are not close are preferably ignored in the calculation of the distance matrix D, since they are most likely not signatures of the same peptide and therefore most likely do not belong to the same cluster.

For example, in FIG. 3B, for each element i, j in temporary matrix 120 where the difference between the PM of peptide spectra i and peptide spectra j is greater than 2 Daltons, the entry is set to a '−'.

A distance matrix D, labeled as 130, is then preferably constructed by calculating the distance between the elements whose entries in the temporary matrix 120 is equal to '+' and inserting the distance into matrix 130, as shown in FIG. 3C. Typically, the distance function chosen is commutative, dij=dji, and thus matrix 130 is symmetric, in which case all relevant distances may be stored only on half of matrix 130, such as the bottom half, and their symmetric values on the other half of matrix 130 are calculated as needed. For descriptive purposes only, matrix 130 is shown with all relevant distances stored in both halves of matrix 130.

Furthermore, matrix 130 is typically very sparsely populated. Matrix 130 is preferably represented as linear array 140, labeled D', in which only elements of matrix 130 that are of interest are stored, such as those elements not marked by a '−' symbol. For example, matrix 130 is preferably represented by linear array 140, D' whose values are: {2, 4, 0, 2, 1, 1, 4, 3, 4, 4, 5, 2, 2}. Access to the elements in D' is preferably performed with the aid of a reference vector 150, labeled 'ref', in which each element in reference vector 150 contains the cumulative sum of the elements of interest up to its corresponding row in matrix 130. Thus, continuing the example presented above, the first element of ref is equal to 0 since there are no elements in the first row of matrix 130 that are of interest. The second element equals 1, since there is one element in the second row of interest. The third element of ref is equal to 3, since there are two elements of interest in the third row of matrix 130 and the cumulative sum of the elements in ref until the third row (the sum of the first and second elements) is equal to 1. In this fashion the reference vector 150 shown in FIG. 3C may be constructed.

The i, j-th element in the matrix 130 may be accessed as follows: If i does not equal j, determine if the element exists in D' by verifying that abs(i−j)<=ref[i]−ref[i−1]. If i is greater than j, return D'[ref[i]+j−i]. If j is greater than i, return D'[ref [j]+i−j]. If i equals j than the distance is 0 by definition, and no access to matrix 130 is required. If the element does not exist in D', return a value that indicates that the element is not to be considered in determining the minimum.

Figure 4A:
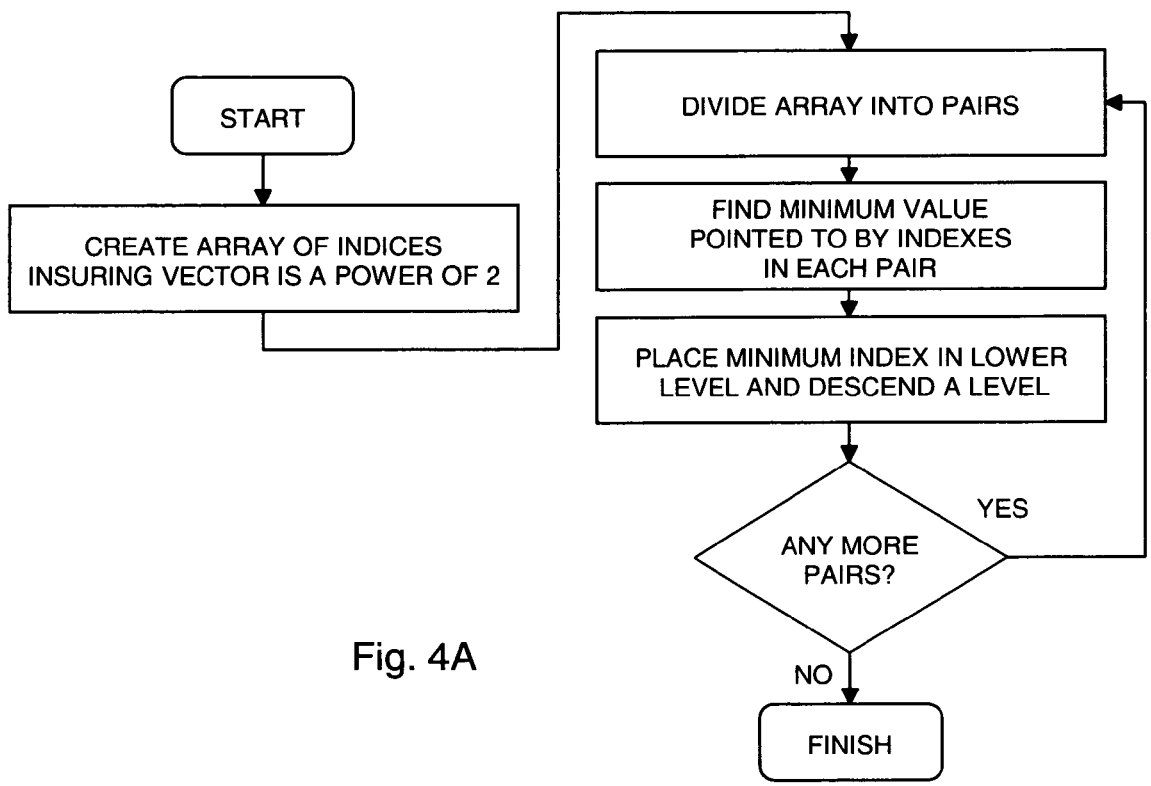
FIG. 4A is a simplified flowchart illustration of a method for finding the minimum in a vector, operative in accordance with an embodiment of the present invention.
Figure 4B:
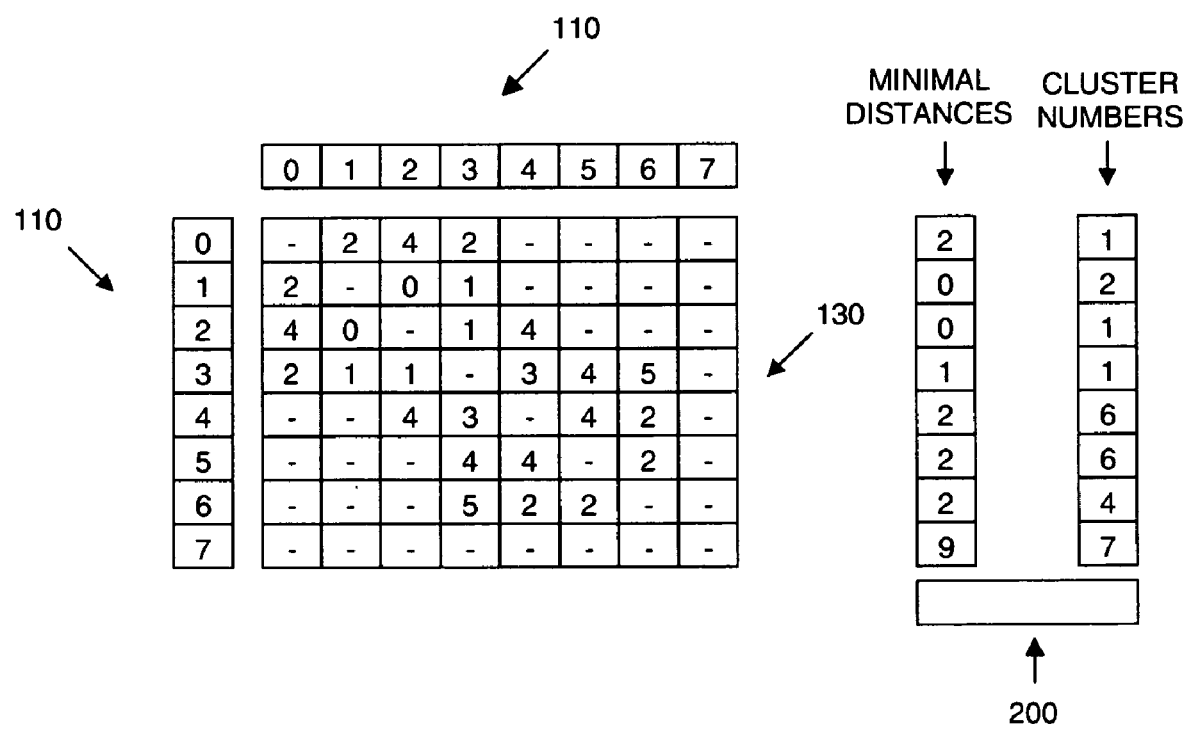
FIG. 4B is a simplified pictorial illustration of an exemplary vector, constructed and operative in accordance with an embodiment of the present invention.
Figure 4C:
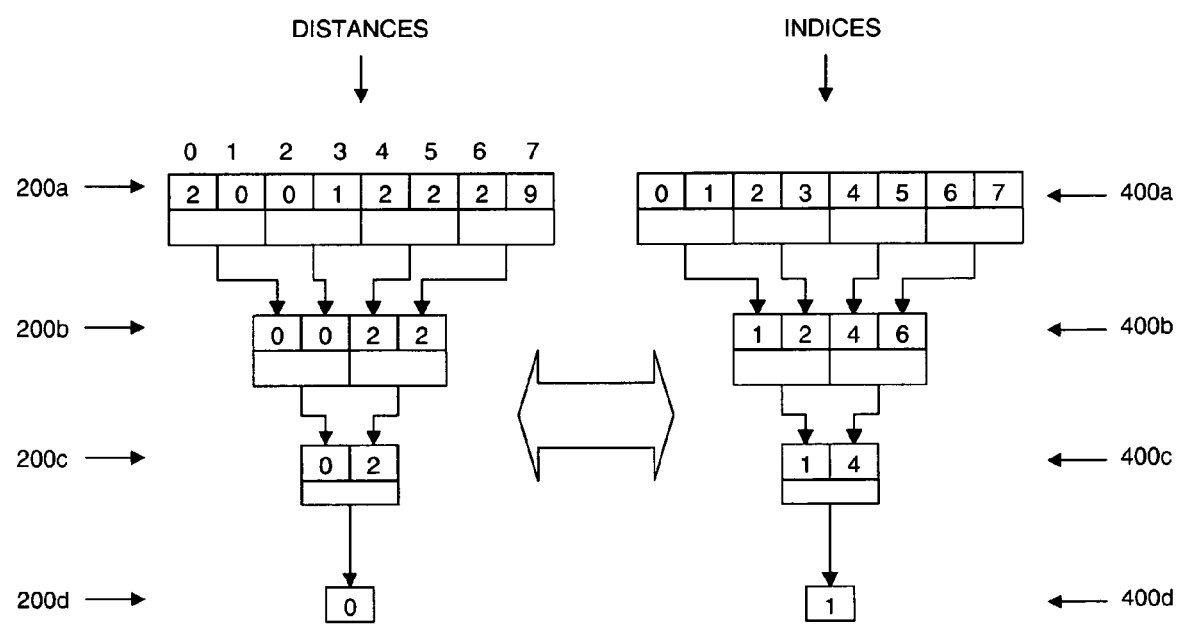
FIG. 4C is a simplified pictorial illustration of a hierarchically ordered vector, constructed and operative in accordance with an embodiment of the present invention.

Reference is now made to FIG. 4A, which is a simplified flowchart illustration of a method for finding the minimum in a vector, operative in accordance with an embodiment of the present invention, FIG. 4B, which is a simplified pictorial illustration of an exemplary vector, constructed and operative in accordance with an embodiment of the present invention, and to FIG. 4C, which is a simplified pictorial illustration of a hierarchically ordered vector, constructed and operative in accordance with an embodiment of the present invention. In the method of FIG. 4A, a vector V, labeled 200 in FIG. 4B, is preferably indirectly ordered by its distance elements to create a hierarchal ordered tree. To facilitate the ordering process, and the updating process as described hereinbelow with reference to FIG. 5A, an array of indices 400 is created, in which each element of array 400 points to a distance component in vector 200. Preferably, array 400 is directly ordered to create a hierarchal tree with the top level of the tree labeled 400a and each subsequent lower level in the tree labeled 400b, 400c and 400d. The hierarchal tree of vector 200a, 200b, 200c and 200d may be referenced from array 400a, 400b, 400c and 400d. The tree is preferably constructed as follows:

1. Insure that the size of V is a power of 2, where V has K^2 elements, and create the highest level of the tree A which contains the indices from 0 to K^2−1
2. Divide current level of A into pairs of elements
3. Find which element in a pair points to a smaller value in V
4. Copy this element to the lower level of the hierarchal tree of A, in its corresponding location. The first pair corresponds to the first element in the lower level of the hierarchal tree, the second pair to the second element and so forth for each pair
5. Are there any more pairs? If not, stop iterative process
6. Descend a level. Go to step 2.

In the example shown in FIG. 4B, row-wise vector 200, which includes the minimum in each row of matrix 130, {2, 0, 0, 1, 3, 4, 2, 9}, and their respective cluster numbers, {1, 2, 1, 1, 6, 6, 4, 7}, is ordered. The distance component of the last element of vector 200 is set to a value that indicates that the element is not to be considered in determining the minimum, such as the value 9, to indicate that the last row of matrix 130 does not include any relevant information for the clustering. This is due to the processing of the rows in matrix 130, described hereinabove with reference to FIG. 3A.

In FIG. 4C, array 400a of indices to vector 200a is constructed and the iterative ordering process described above performed, the index of each element in vector 200a has been included above vector 200a for additional clarity. In the first iteration, array 400a is divided into element pairs, and the index of the minimum distance found in of each pair is placed in the lower level array 400b. Thus, the index of the minimum of the first pair {2,0} equals {1} and is placed in the first entry of the array 400b, the index of the minimum of the second pair {0, 1} equals {2} and is placed in the second entry in the array 400b, the index of the minimum of the third pair {2,2} equals {4} and is placed in the third entry in the array 400b and the index of the minimum of the fourth pair {2, 9} equals {6} and is placed in the fourth entry in the array 400b. Thus, at the conclusion of the first iteration, array 400b includes the elements {1, 2, 4, 6}. For descriptive purposes, FIG. 4C shows the corresponding level in vector 200b, which has the values {0, 0, 2, 2}.

In the second iteration, array 400b is divided into element pairs and the index of the minimum of each pair is placed in the lower level array 400c. Thus, the index of the minimum of the first pair {0, 0} equals {0} and is placed in the first entry of array 400c, and the index of the minimum of the second pair {2, 2} equals {2} and is placed in the second entry array 400c. At the conclusion of the second iteration array 400c includes the elements {0, 2}. For descriptive purposes, FIG. 4C shows the corresponding level in vector 200c, which has the values {0, 2}.

In the third iteration the index of the minimum of the single pair {0, 2}, which is equal to {0} and which/whose index is {1}, are/is placed in the lower level array 400d. The global minimum, may now be determined by identifying the root of the hierarchical tree, array 400d, being the lowest node of the tree. The value of the global minimum in this example is {1}, which points to the minimum in vector 200, whose components include the distance and the cluster number of the nearest cluster {0, 2}.

Thus, in the above example, cluster number 1 has been determined to be nearest to cluster number 2, with a distance of 0 separating them. The next phase of the clustering algorithm as described hereinabove with reference to FIG. 2B is to merge the two nearest clusters, cluster number 1 and 2, in the first iteration as demonstrated hereinbelow with reference to FIG. 5B.

Figure 5A:
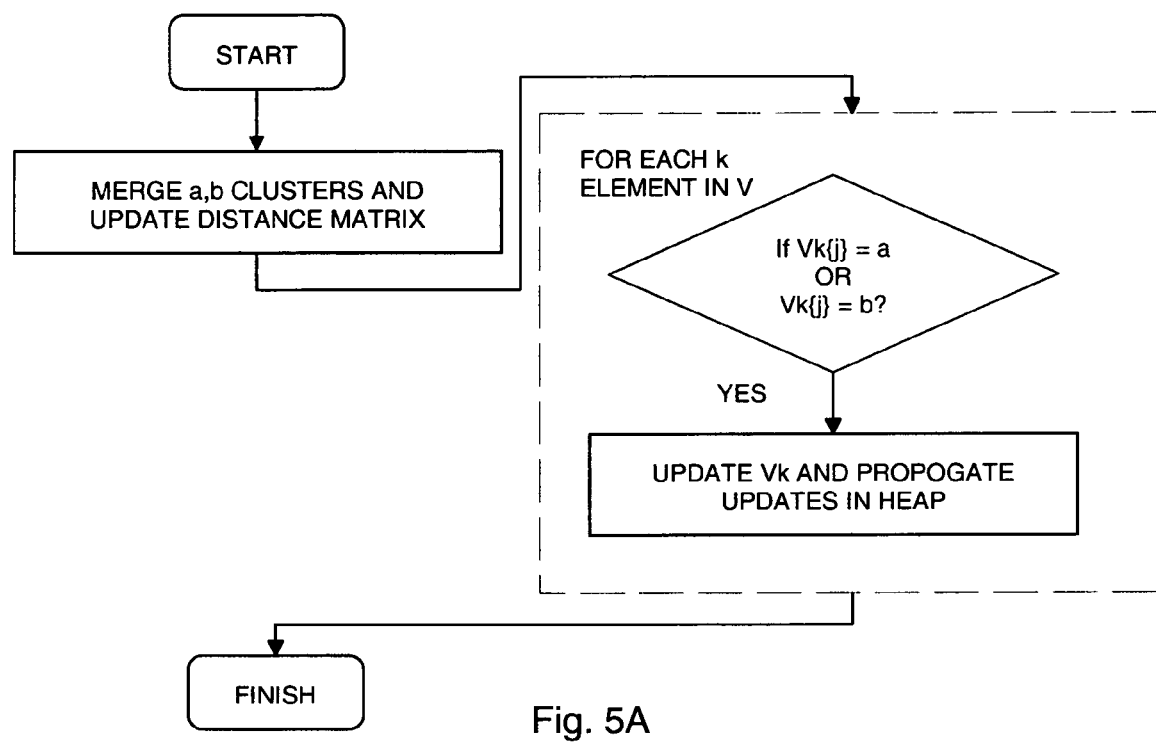
FIG. 5A is a simplified flowchart illustration of a method of updating a row-wise minimum vector of a distance matrix, operative in accordance with an embodiment of the present invention.
Figure 5B:
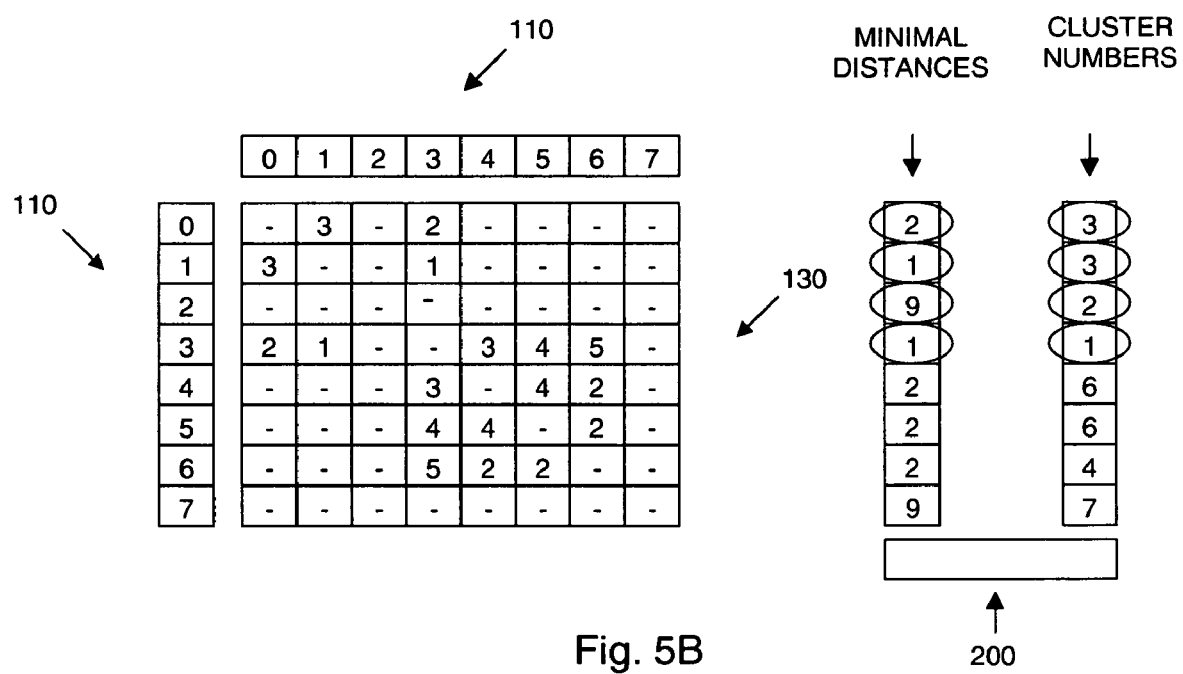
FIG. 5B is exemplary distance matrix and row-wise vector, constructed and operative in accordance with an embodiment of the present invention.
Figure 5C:
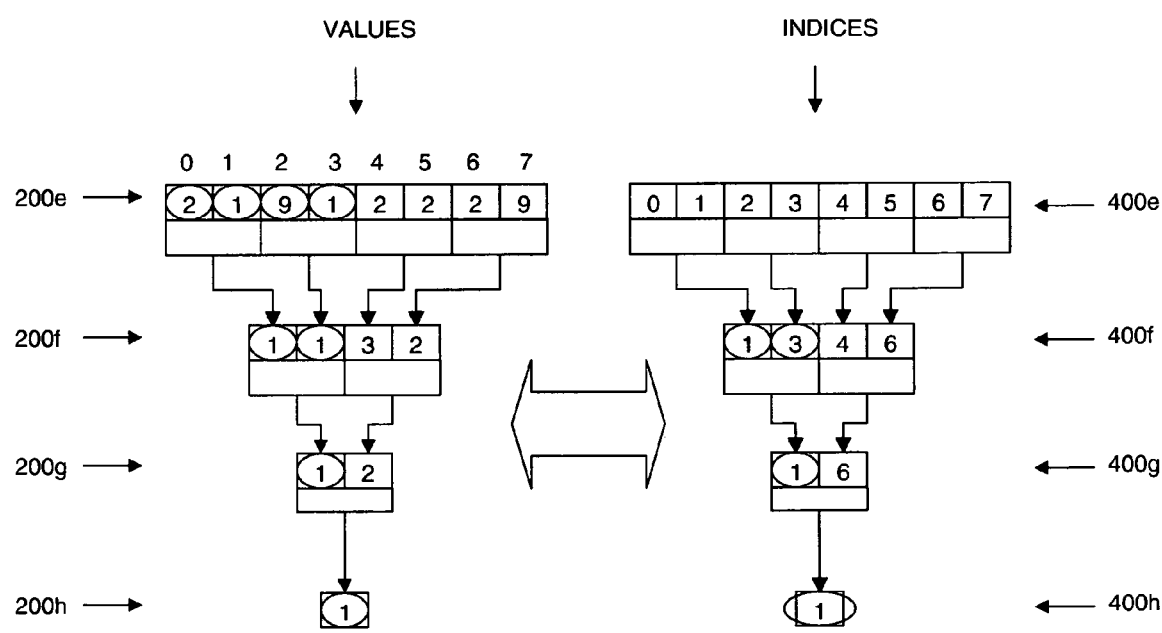
FIG. 5C is a simplified pictorial illustration of an exemplary updated row-wise minimum vector of a distance matrix, constructed and operative in accordance with an embodiment of the present invention.
Figure 6A:
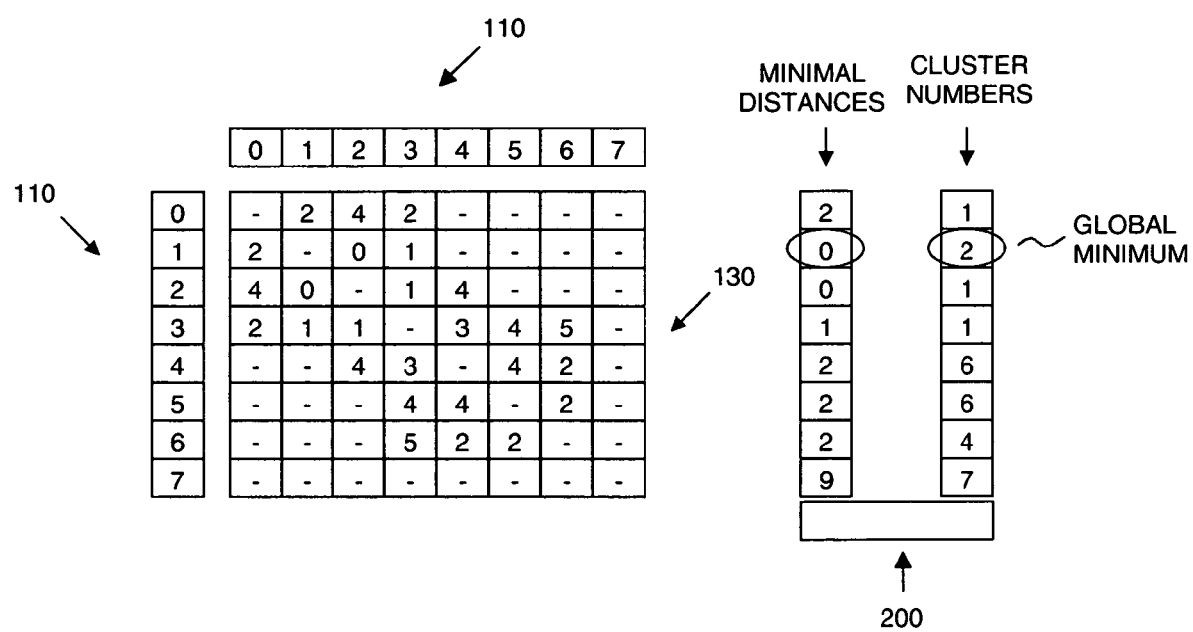
FIGS. 6A through 6E are exemplary distance matrices and row-wise vectors, constructed and operative in accordance with an embodiment of the present invention.
Figure 6B:
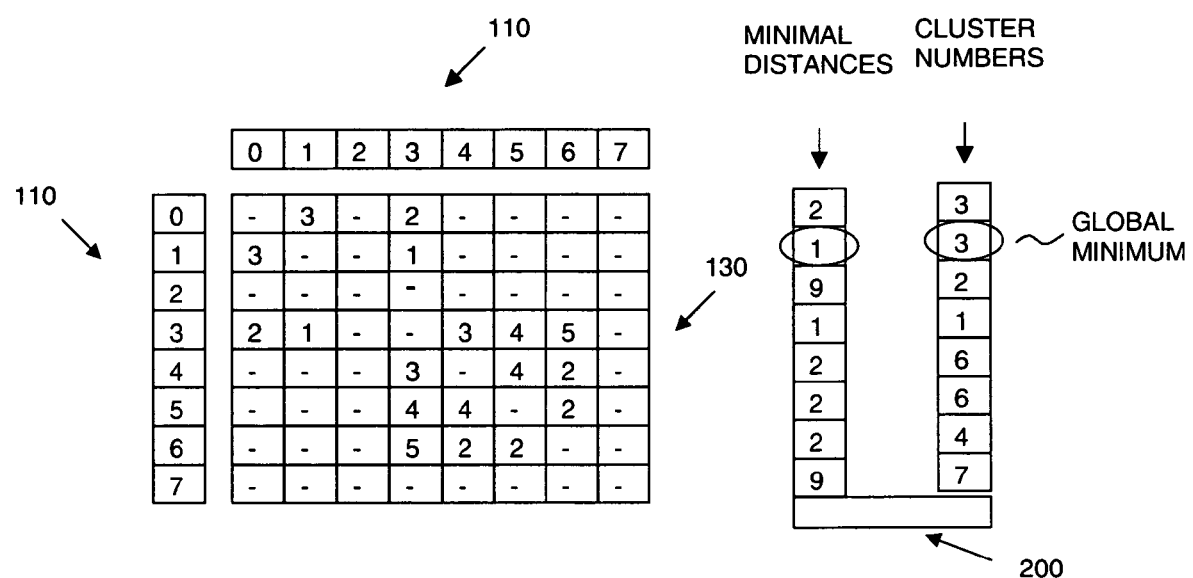
Figure 6C:
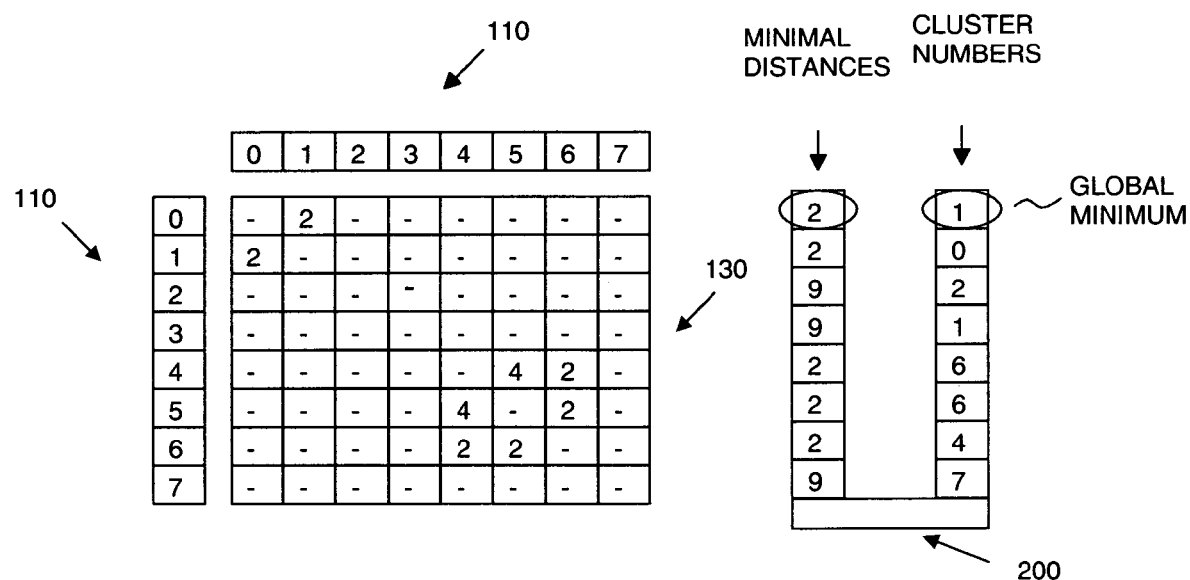
Figure 6D:
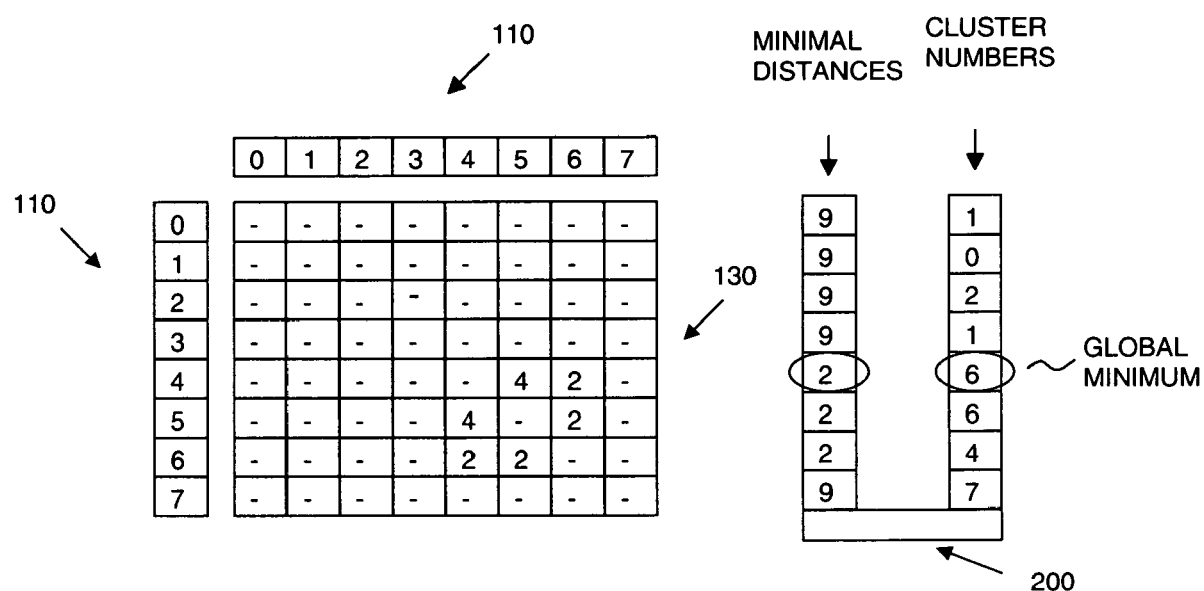
Figure 6E:
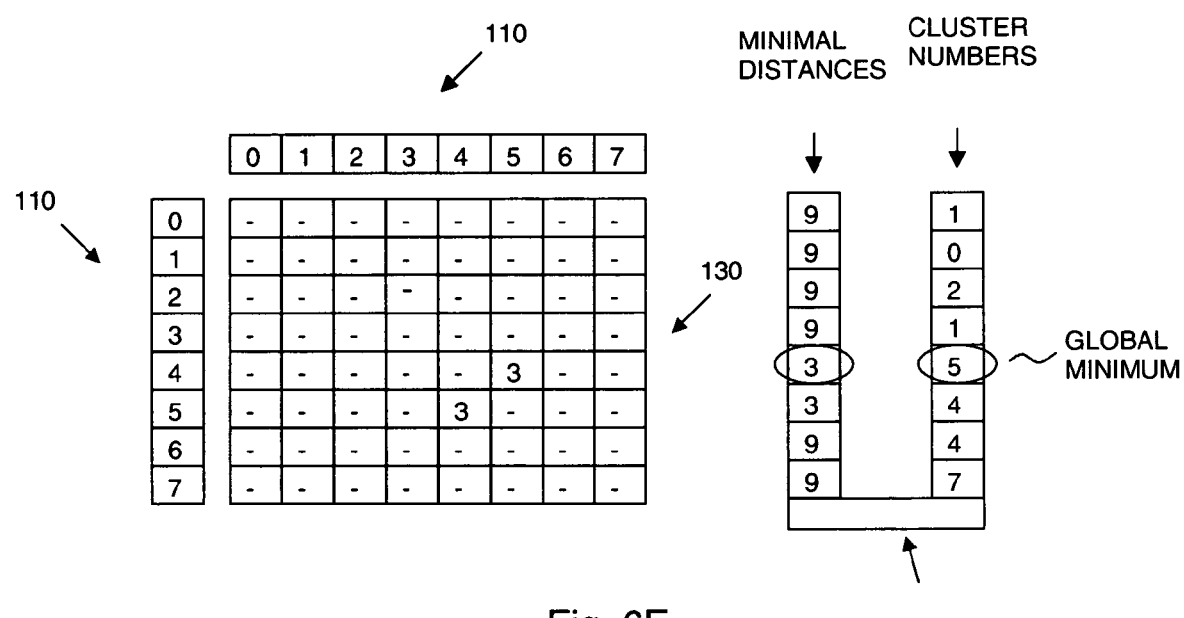

Reference is now made to FIG. 5A, which is a simplified flowchart illustration of a method of updating a row-wise minimum vector of a distance matrix, operative in accordance with an embodiment of the present invention, FIG. 5B, which is exemplary distance matrix and row-wise vector, constructed and operative in accordance with an embodiment of the present invention, and to FIG. 5C, which is a simplified pictorial illustration of an exemplary row-wise minimum vector of a distance matrix, constructed and operative in accordance with an embodiment of the present invention. In the method of FIG. 5A, a previously ordered row-wise minimum vector V of a distance matrix, such as the vector described above with reference to FIG. 4B, is updated prior to determining the global minimum of the distance matrix by finding the minimum of any of the rows in distance matrix 130 where the distance between the cluster as represented by the row and either of the merged clusters was the smallest relative to the distance between the cluster and any of the other clusters.

Assuming that two clusters, a and b, were merged to create a new cluster as described above with reference to FIG. 2B, and the newly created cluster replaces cluster a in distance matrix 130, the row-wise minimum vector V of a distance matrix is preferably updated as follows:

1. Replace the distance value in $V_a$ with the new minimum in row a and set the column corresponding to the cluster numbers in V to the cluster number of the minimum value.
2. Replace the distance value in $V_b$ with a value that indicates that the element is not to be considered in determining the global minimum, such as 9.
3. For each element k in V, if the component that stores the cluster number in $V_k$ equals either of the merged clusters a or b, then update $V_k$. This is preferably done if and only if the index stored in the element $V_k$, i.e. the second half of the paired element $V_k$, equals a or b. Continuing with the example described above, as can been seen in FIG. 4B there are four elements in vector 200 whose cluster number equals either 1 or 2. Two of those elements correspond to clusters that have been merged, leaving two elements which do not correspond to merged clusters, and need to be updated.
4. Iteratively propagate the updates through each hierarchal level.

In the example shown in FIG. 5B, clusters 1 and 2 in distance matrix 130 have been merged in the first iteration into the elements of cluster 1. The rows and columns associated with cluster 1 are updated by calculating the averages of each pair of corresponding elements in corresponding rows and columns of clusters 1 and 2. If one of the elements in the pair is marked with a '−' symbol, the corresponding value in cluster 1 is set to '−'. The values of the rows and columns of cluster 2 may be marked as empty with a '−' symbol.

In the example shown in FIG. 5C the first four elements in vector 200 have been modified. The array of indices, array 400, may now be updated as described above, with the modifications propagated to each lower level in the heap, where at each iteration only the pairs that are affected by the modification are preferably checked. Thus, in the example shown in FIG. 5C, at the first iteration only the first and second set of pairs in array 400e, {0, 1} and {2, 3}, are compared, and the index to the minimums in vector 200 are placed into the first and second elements of array 400f. At the second iteration, only the first pair {1, 3} of array 400f is checked, and the index to the minimum in vector 200 is placed into the first element of array 400g. At the final iteration, the single pair found in array 400g is checked, and the index to the minimum, {1}, is placed in array 400h, where it is designated as the global minimum.

The second element in vector 200, indexed by the minimum found in the above steps, contains the two components whose elements include the distance and the cluster number of the nearest cluster {1, 3}. Thus, cluster number 1 and cluster number 3 may now be merged. Processing may continue as described hereinabove with reference to FIG. 2B, until the stop condition is met, an example of which is described below with reference to FIGS. 6A through 6E. The peptide spectra for each cluster may then be prepared for further identification.

Figure 7A:
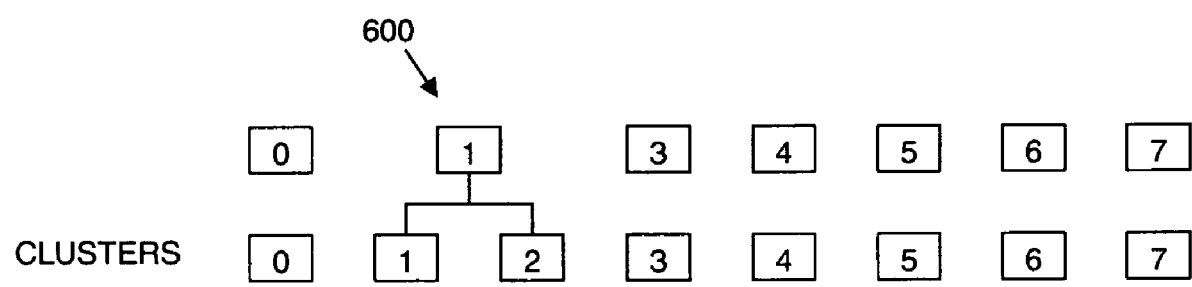
FIGS. 7A through 7E are exemplary dendrograms, constructed and operative in accordance with an embodiment of the present invention.

Reference is now made to FIGS. 6A through 6E, which is an exemplary set of distance matrices, row-wise vectors and dendrograms, constructed and operative in accordance with an embodiment of the present invention. In the example described above with reference to FIG. 5B, in the first iterative step the global minimum of distance matrix 130 is calculated as described hereinabove with reference to FIG. 4A. In the example shown in FIG. 6A, the global minimum is determined to be the second pair of elements in vector 200, {0, 2}, indicating that the two nearest clusters in distance matrix 130 are clusters '1' and '2'. These two clusters are then merged to create a new cluster 1, as described hereinabove with reference to FIG. 5A, labeled 600, shown in the dendrogram in FIG. 7A. Cluster 600 represents the two original peptide spectra that formed clusters 1 and 2, and hence the dendrogram indicates a similarity between the peptide spectra 1 and 2.

Figure 7B:
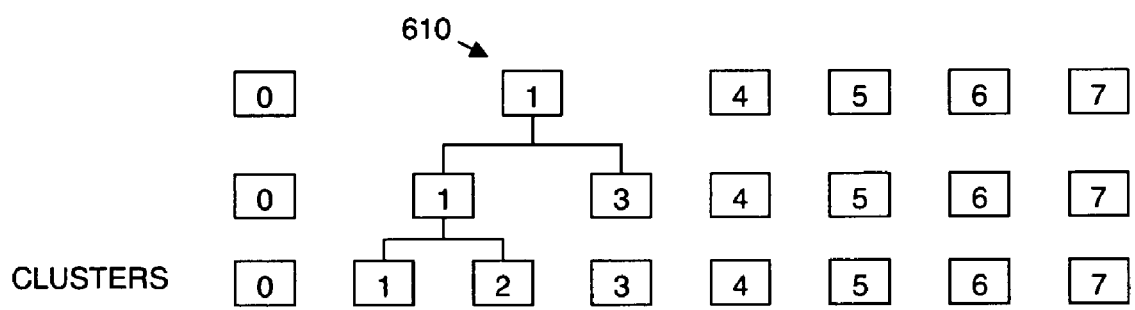

In the second iterative step, the global minimum of distance matrix 130 is calculated as described hereinabove with reference to FIG. 4A. In the example shown in FIG. 6B, the global minimum is determined to be the second pair of elements in vector 200, {1, 3}, indicating that the two nearest clusters in distance matrix 130 are clusters '1' and '3'. These two clusters are then merged to create a new cluster 1, as described hereinabove with reference to FIG. 5A. The newly formed cluster labeled 610 is shown in the dendrogram in FIG. 7B. Cluster 610 represents the three original peptide spectra that formed clusters 1, 2 and 2, and hence the dendrogram indicates a similarity between the peptide spectra 1, 2 and 3.

Figure 7C:
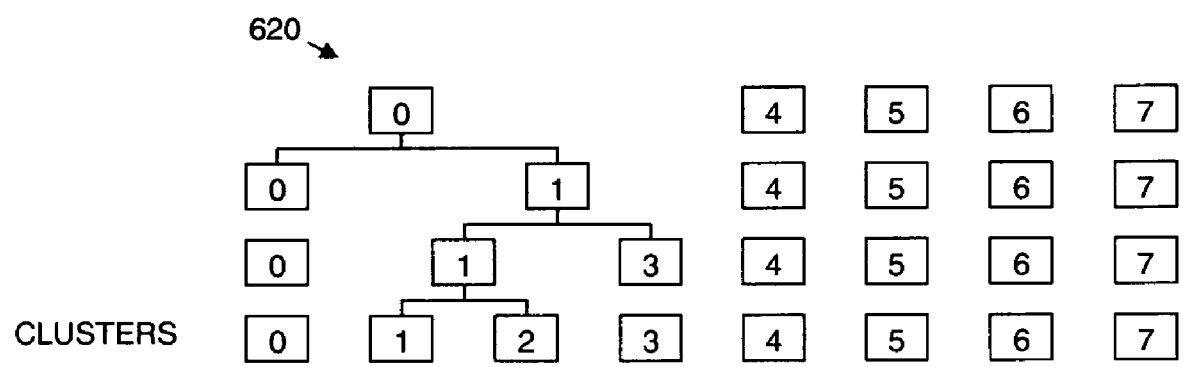

In the third iterative step, the global minimum of distance matrix 130 is calculated as described hereinabove with reference to FIG. 4A. In the example shown in FIG. 6C, the global minimum is determined to be the first pair of elements in vector 200, {2, 1}, indicating that the two nearest clusters in distance matrix 130 are clusters '0' and '1'. These two clusters are then merged to create a new cluster 0, as described hereinabove with reference to FIG. 5A. The newly formed cluster labeled 620 is shown in the dendrogram in FIG. 7C. Cluster 620 represents the four original peptide spectra that formed clusters 0, 1, 2 and 3, and hence the dendrogram indicates a similarity between the peptide spectra 0, 1, 2 and 3.

Figure 7D:
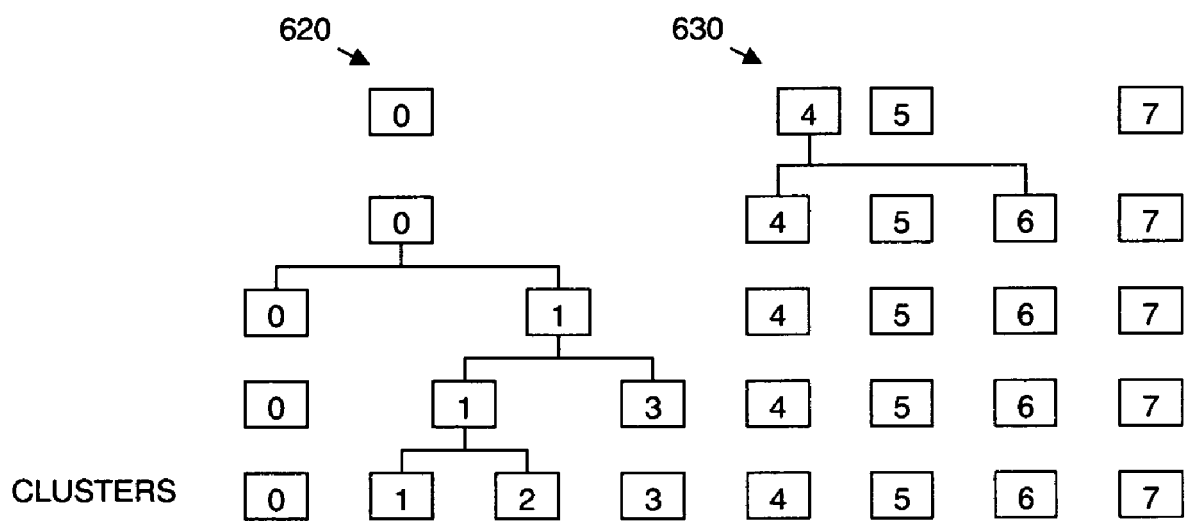

In the fourth iterative step, the global minimum of distance matrix 130 is calculated as described hereinabove with reference to FIG. 4A. In the example shown in FIG. 6D, the global minimum is determined to be the fifth pair of elements in vector 200, {2, 6}, indicating that the two nearest clusters in distance matrix 130 are clusters '4' and '6'. These two clusters are then merged to create a new cluster 4, as described hereinabove with reference to FIG. 5A. The newly formed cluster labeled 630 is shown in the dendrogram in FIG. 7D. Cluster 630 represents the two original peptide spectra that formed clusters 4 and 6, and hence the dendrogram at the fourth iteration indicates a similarity between the peptide spectra 0, 1, 2 and 3, represented by cluster 620 and a similarity between the peptide spectra 4 and 6, represented by cluster 630.

Figure 7E:
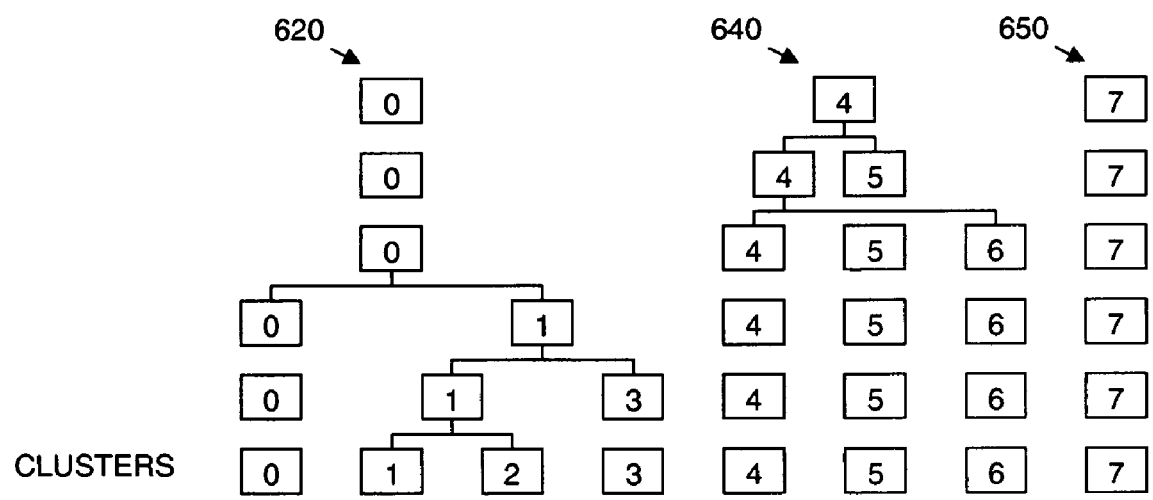

In the fifth iterative step, the global minimum of distance matrix 130 is calculated as described hereinabove with reference to FIG. 4A. In the example shown in FIG. 6E, the global minimum is determined to be the fifth pair of elements in vector 200, {3, 5}, indicating that the two nearest clusters in distance matrix 130 are clusters '4' and '5'. These two clusters are then merged to create a new cluster 4, as described hereinabove with reference to FIG. 5A. The newly formed cluster labeled 640 is shown in the dendrogram in FIG. 7E. Cluster 640 represents the three original peptide spectra that formed clusters 4, 5 and 6, and hence the dendrogram at the fourth iteration indicates a similarity between the peptide spectra 0, 1, 2 and 3, represented by cluster 620 and a similarity between the peptide spectra 4, 5 and 6, represented by cluster 640. In addition the peptide spectra represented by cluster 7, labeled 650 is not identified with any other cluster.

Thus at the conclusion of the preparation steps, the eight original peptide spectra are organized into three clusters, cluster 620, cluster 640 and cluster 650. Each of the peptide spectra for each cluster may then be submitted to peptide identifier 40 for identification.

It is appreciated that one or more of the steps of any of the methods described herein may be omitted or carried out in a different order than that shown, without departing from the true spirit and scope of the invention.

While the methods and apparatus disclosed herein may or may not have been described with reference to specific computer hardware or software, it is appreciated that the methods and apparatus described herein may be readily implemented in computer hardware or software using conventional techniques.

While the present invention has been described with reference to one or more specific embodiments, the description is intended to be illustrative of the invention as a whole and is not to be construed as limiting the invention to the embodiments shown. It is appreciated that various modifications may occur to those skilled in the art that, while not specifically shown herein, are nevertheless within the true spirit and scope of the invention.

What is claimed is:

1. A method for preparing peptide spectra for identification, the method comprising:
    a) populating a matrix with a plurality of clusters of a plurality of peptide spectra, wherein each of said clusters is represented in both a different row of said matrix and a different column of said matrix, thereby resulting in a symmetric matrix;
    b) finding the minimum of each of said clusters in said matrix;
    c) populating a vector with said minima of said clusters wherein each element in said vector corresponds to one of said clusters;
    d) finding the global minimum of said matrix as being the minimum of said vector;
    e) merging two of said clusters identified by said global minimum into a merged cluster; and
    f) providing said merged cluster for identification of at least one peptide associated with said merged cluster.

2. A method according to claim 1 wherein said populating step a) comprises:
    representing said plurality of peptide spectra as a set of multidimensional vectors;
    ordering said multidimensional vectors;
    determining the closeness between any two of said ordered vectors in accordance with a measure of closeness;
    determining the distance between any two of said ordered vectors using a distance function where said vectors are close to each other in accordance with said measure of closeness; and
    constructing said matrix from said distances.

3. A method according to claim 2 wherein said ordering step comprises ordering said vectors according to their precursor (parent) mass (PM) of their associated peptide.

4. A method according to claim 3 wherein said determining closeness step comprises determining that said two vectors are close where their masses are within 2 Daltons of each other.

5. A method according to claim 1 wherein said finding step d) comprises:
    ordering said elements in said vector in hierarchical order; and
    identifying the root of said hierarchy as said global minimum.

6. A method according to claim 5 and further comprising:
    g) finding the minimum of any of said clusters in said matrix where said distance between said cluster and either of said merged clusters was the smallest relative to the distance between said cluster and any other of said clusters;
    h) updating any of said elements in said vector for which a minimum was found in step g) for said cluster corresponding to said element; and
    i) reordering said updated elements in said vector in hierarchical order.

7. A method according to claim 1 and further comprising:
    g) finding the minimum of any of said clusters in said matrix where said distance between said cluster and either of said merged clusters was the smallest relative to the distance between said cluster and any other of said clusters; and
    h) updating any of said elements in said vector for which a minimum was found in step g) for said cluster corresponding to said element.

8. A method according to claim 1 wherein each of said vector elements is associated with an index of any of said clusters for which said minimum was found with respect to said cluster to which said vector element corresponds.

* * * * *